United States Patent
Adams et al.

(10) Patent No.: US 8,551,004 B2
(45) Date of Patent: Oct. 8, 2013

(54) DUAL MODE ULTRASOUND TRANSDUCER

(75) Inventors: Darwin Adams, Lexington, MA (US); Andrew Robinson, Bellevue, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 334 days.

(21) Appl. No.: 12/678,346

(22) PCT Filed: Aug. 27, 2008

(86) PCT No.: PCT/IB2008/053456
§ 371 (c)(1),
(2), (4) Date: Nov. 8, 2010

(87) PCT Pub. No.: WO2009/031079
PCT Pub. Date: Mar. 12, 2009

(65) Prior Publication Data
US 2011/0046484 A1    Feb. 24, 2011

Related U.S. Application Data

(60) Provisional application No. 60/969,818, filed on Sep. 4, 2007.

(51) Int. Cl.
*A61B 8/14* (2006.01)
(52) U.S. Cl.
USPC .......................................... 600/459; 600/437
(58) Field of Classification Search
USPC .................................................. 600/437–469
See application file for complete search history.

(56) References Cited

U.S. PATENT DOCUMENTS

| | | | |
|---|---|---|---|
| 5,261,408 A * | 11/1993 | Maslak et al. | 600/447 |
| 5,488,956 A | 2/1996 | Bartelt et al. | |
| 5,902,241 A | 5/1999 | Seyed-Bolorforosh et al. | |
| 6,055,861 A * | 5/2000 | Banta et al. | 73/626 |
| 6,104,673 A | 8/2000 | Cole et al. | |
| 6,106,472 A * | 8/2000 | Chiang et al. | 600/447 |
| 6,866,632 B1 * | 3/2005 | Chou et al. | 600/443 |
| 2006/0058672 A1 * | 3/2006 | Klepper | 600/447 |

FOREIGN PATENT DOCUMENTS

WO    03024625 A    3/2003

* cited by examiner

*Primary Examiner* — Sanjay Cattungal

(57) ABSTRACT

A curved array ultrasound transducer is described which is usable in both sector and curved linear modes. The transducer includes a central portion (40) of elements and lateral portions (44) of elements on either side of the central portion. In the sector mode the central portion of elements is operated to perform phased array scanning. In the curved linear mode both the central and lateral portions of elements are operated to perform curved linear array scanning. The transducer elements of the central portion have a finer pitch than the pitch of the transducer elements of the lateral portions. In the sector mode, the elements of the central portion are operated individually, and in the curved linear mode the transducer elements of the central portion are operated in pairs. In the sector mode, the number of transducer elements of the central portion that participate in the active aperture of the transducer may be varied according to the number of transducer elements in acoustic contact with the patient.

18 Claims, 7 Drawing Sheets

DUAL MODE ULTRASOUND TRANSDUCER

This invention relates to ultrasound systems, and, more particularly, to transducers for ultrasound systems.

In ultrasound diagnostic imaging, ultrasonic energy is emitted into a patient's body. The reflected energy is detected and processed to form images indicating the density and boundaries of tissue and the location and velocity of blood flow within the patient. Ultrasonic signals are typically emitted from a transducer including an array of individual piezoelectric transducer elements that also serve to detect the reflected signals.

Various transducers and scanning modes may be used to emit and receive the ultrasonic signals. In phased array imaging, multiple transducer elements emit signals having a phase and amplitude relationship such that they combine to form a single beam that can be steered to scan a pie-shaped sector viewing area. Sector mode imaging is particularly useful for imaging beneath a patient's ribs inasmuch as the beams can originate from a common vertex aimed between the patient's ribs, rather than a broader aperture emitting and receiving signals that can be blocked by the ribs.

In linear array scanning, a array of transducer elements sequentially emits signals from different groups of elements and receives signals from a viewing area within a patient. Linear arrays are typically used in applications requiring a wide view of a region close to the skin surface, and where acoustic access to the region of interest is not obstructed. Linear arrays are either flat or curved. A flat linear array provides a rectangular or trapezoidal field of view, while a curved linear provides a field of view that fans out due to the curvature of the array.

In practice, a technician will often need to have multiple transducers in order to adequately image different anatomies of a patient, which increases the cost of the ultrasound system. The technician will also need to switch the system operation from one transducer to another, which takes time. Inasmuch as transducers are used with a sound-conducting gel applied to the patient, each transducer therefore needs to be cleaned after use, requiring more time.

In view of the foregoing, it would be advantageous to provide an ultrasound transducer suitable for performing both sector and curved linear array scanning.

In accordance with the principles of the present invention, an ultrasound system includes a transducer having a face with a central portion and lateral portions on either side of the central portion. A first plurality of transducer elements are disposed on the central portion and a second plurality of transducer elements disposed on the lateral portions. The first plurality of transducer elements have a first, fine pitch for sector mode and the second plurality of transducer elements have a second, coarser pitch for linear mode. The array can be either curved or planar.

In sector mode, a beamformer is coupled to operate the transducer elements of the first plurality for phased array imaging. In linear mode, the beamformer is coupled to operate the transducer elements of both groups. In accordance with a further aspect of the present invention, pairs of adjacent transducers of the first plurality may be operated in tandem so that the transducer will exhibit a common element pitch over the full operable aperture.

In another aspect of the invention, the number of transducer elements of the first plurality that are activated in sector mode is varied according to the number of transducer elements in contact with the patient's skin.

In another aspect of the invention, a mode selection switch is provided enabling a user to switch between linear and sector modes.

Figure 1:
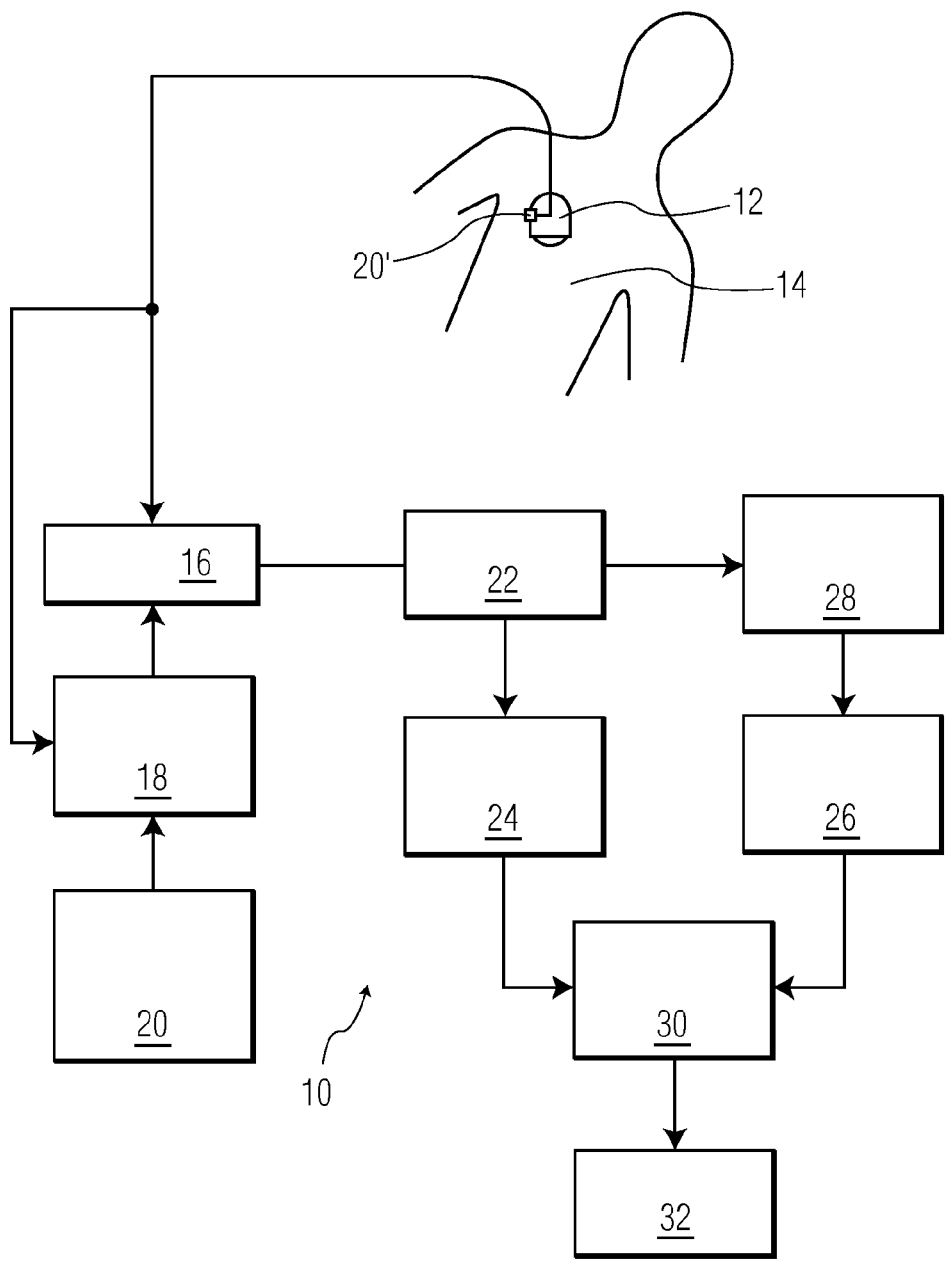
FIG. 1 is a block diagram of an ultrasound system in accordance with an embodiment of the present invention.

Referring to FIG. 1, an ultrasound system 10 includes a transducer 12 having a number of transducer elements suitable for transmitting ultrasonic signals into a patient and receiving echo signals. The transducer elements are preferably piezoelectric transducer elements. The transducer 12 is coupled to a beamformer 16 which is controlled by a beamformer controller 18. The beamformer 16 controls the phase and amplitude of excitation signals applied to the elements of the transducer 12 to create ultrasound beams scanning a viewing area within a patient. The beamformer 16 also relatively delays the phase of signals received by the transducer elements to bring the signals into phase coherence and then sums them. In the illustrated embodiment, a mode selector switch 20 is coupled to the beamformer controller 18 so that the user can set the beamformer operation for scanning with the transducer 12 in a sector mode, linear mode, and other operational modes. In other embodiments the mode selector switch 20' is located on the case of the transducer. In yet other embodiments, the mode selector switch is provided by a graphical user interface coupled to the beamformer controller 18.

The output of the beamformer 16 is filtered to extract information from the echo signal. In the illustrated embodiment, a quadrature bandpass filter 22 is used. The output of the filter 22 is provided to one or both of a B-mode processor 24 and a Doppler processor 26. The B-mode processor 24 processes the data to produce information regarding the structure of the tissue that reflected the excitation signal. The Doppler processor 26 processes the data to extract information regarding the velocity of blood flow within the viewing area. Data provided to the Doppler processor 26 may be stored in an ensemble store 28 before being processed by the Doppler processor 26 until sufficient samples of the viewing area have been acquired to form a Doppler image. The outputs of the B-mode processor 24 and Doppler processor 26 are provided to an image processor 30 that creates B-mode and Doppler images of the desired image format, which are then displayed on a display 32.

Figure 2A:
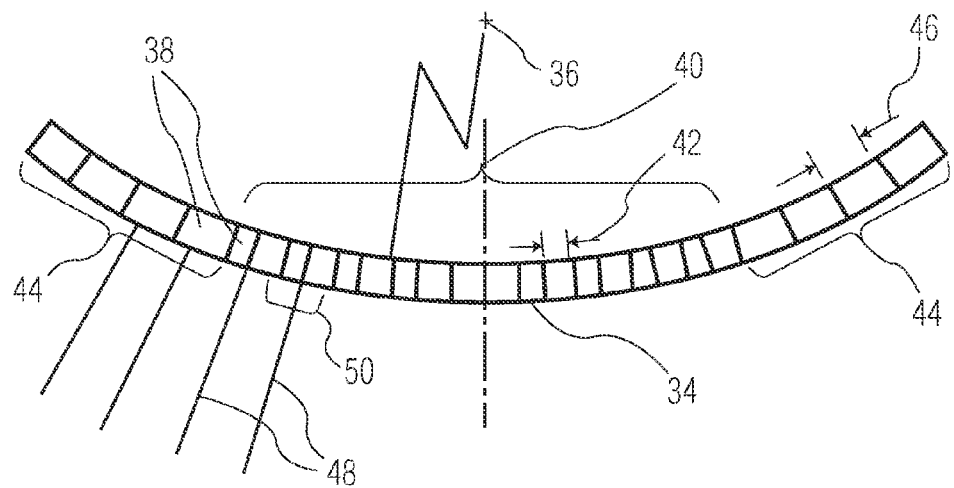
FIGS. 2A and 2B are schematic diagram of a transducer face in accordance with an embodiment of the present invention.
Figure 2B:
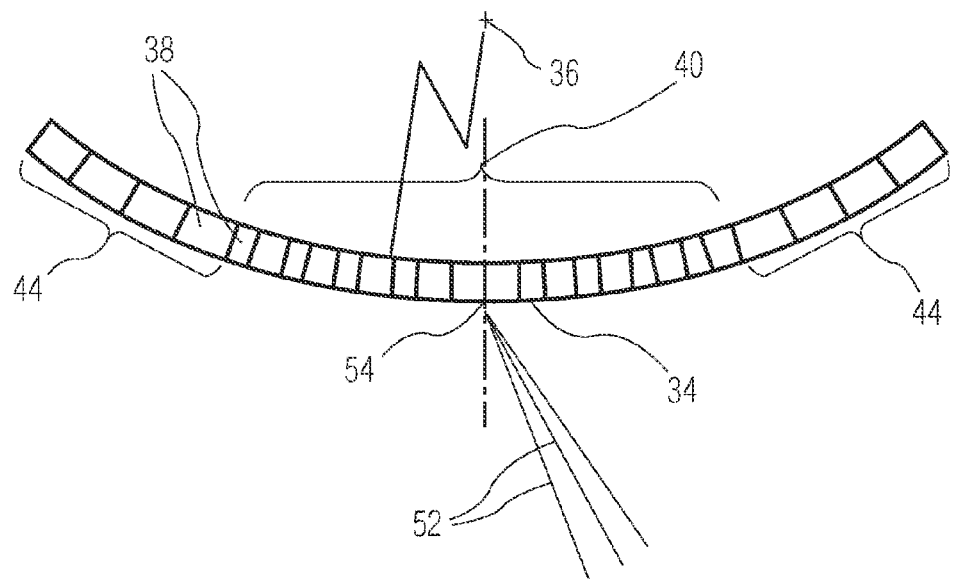

Referring to FIGS. 2A and 2B, the transducer 12 has a face 34 that is convex, having a center of curvature 36 located behind the face 34 and having a plurality of transducer elements 38 distributed along the face 34. The transducer elements 38 located on a central portion 40 of the face 34 have a first pitch 42 and the transducer elements 38 located on lateral portions 44 on either side of the central portion 40 have a second pitch 46 that is greater than the first pitch. In a preferred embodiment, the second pitch 46 is twice the first pitch 42. The combined number of transducer elements 38 on the lateral portions 44 may be equal to one half the number of transducer elements 38 on the central portion 40. The different pitches in the central portion 40 and the lateral portions 44 may be obtained by dicing a piezoelectric crystal at different lateral increments along the face 38.

The transducer elements emit an ultrasound wave with a wavelength $\lambda$. The first pitch 42 may be less than or about equal to $\lambda/2$ whereas the second pitch 46 is less than or about equal to $\lambda$. The different pitches 42, 46 facilitate use of the transducer 12 to perform different types of ultrasound scans.

Referring specifically to FIG. 2A, in a linear scanning mode, the transducer elements 38 are activated sequentially to emit ultrasound beams 48 normal to the face 34. In the linear mode, the transducer elements 38 in the central portion 40 are preferably excited in pairs 50 such that the angular distribution of ultrasound beams 48 is constant.

Referring specifically to FIG. 2B, in a phased array beam-steering mode, the excitation signals applied to the finer pitched elements 38 have phases and amplitudes chosen such that the ultrasound signals emitted from the elements 38 combine to form a focused beam 52 during each transmission. The phases and amplitudes are varied to change the angle of each beam 52 and perform a sector scan of the viewing area. In the illustrated embodiment, the beams 52 extent from an apex 54 located at the face 34 of the transducer. However, the apex 54 may be located at other positions by changing the steering angle, such as in front or behind the face 34. In a preferred embodiment, only the transducer elements 38 of the central portion 40 are used to generate the beams 52 in the beam-steering mode. The finer pitch 42 in the central portion 40 advantageously allows for a greater range of steering angles as compared to a larger pitch without creating grating or significant side lobes or other artifacts that degrade image quality.

Figure 3:
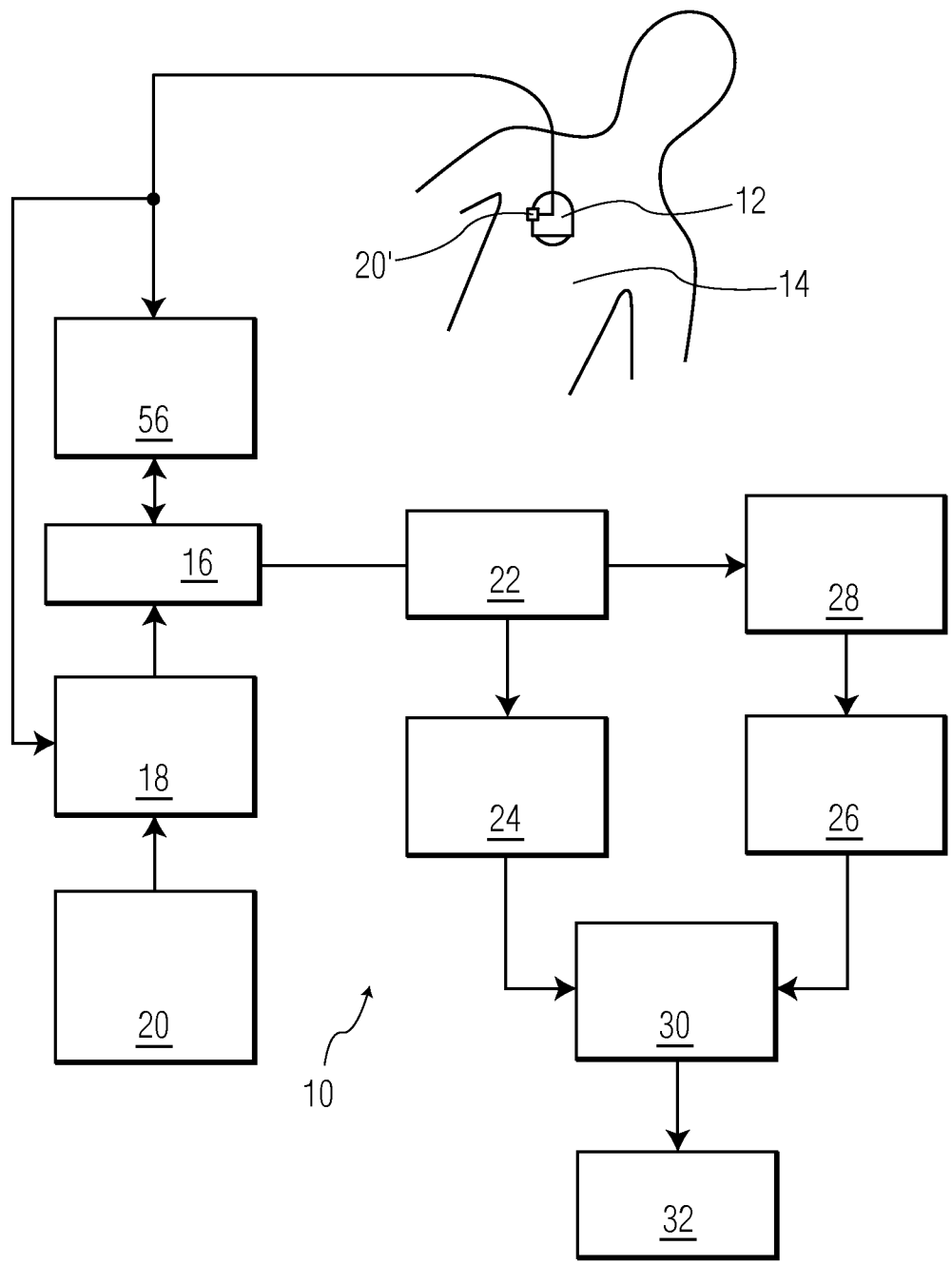
FIG. 3 is a schematic block diagram of an alternative embodiment of an ultrasound system in accordance with an embodiment of the present invention.

Referring to the embodiment of FIG. 3, a switch matrix 56 is interposed between the beamformer 16 and the elements of transducer 12. The switch matrix 56 changes the coupling between signal lines of the beamformer 16 and the transducer elements 38 of the transducer 12 according to a mode selected by the operator. In an alternative embodiment, the signals applied to the transducer elements 38 are controlled programmatically to switch between modes, such as by the beamformer controller 18, without changing the coupling between the beamformer 16 and the transducer elements 38.

Figure 4A:
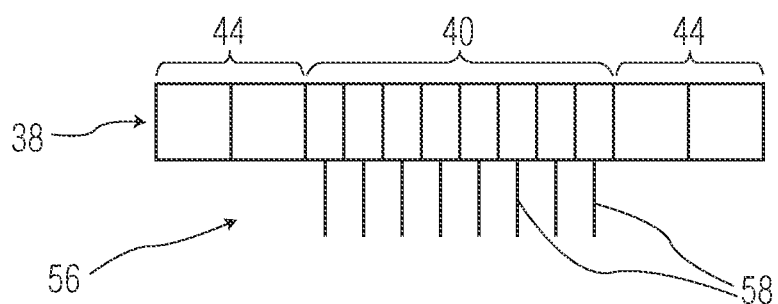
FIGS. 4A and 4B are schematic diagrams of control lines coupled to transducer elements in accordance with an embodiment of the present invention.
Figure 4B:
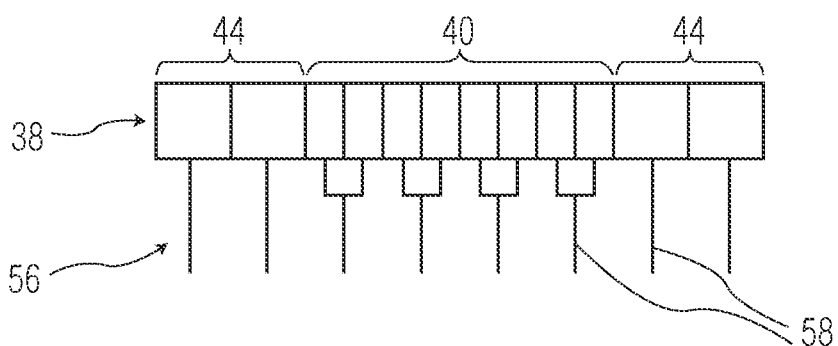

For example, referring to FIG. 4A, the switch matrix 56 may couple control lines 58 from the beamformer 16 to individual transducer elements 38 of the central portion 40 in the sector mode. Referring to FIG. 4B, in the linear mode, the switch matrix 56 couples the control lines 58 to the transducer elements 38 of the lateral portions 44 and to pairs 50 of transducer elements 38 in the central portion 40. In the embodiment of FIGS. 4A and 4B, the number of control lines 58 is less than the total number of transducer elements 38. In the illustrated embodiment, the number of control lines 58 is equal to the number of transducer elements 38 in the central portion, which is two thirds of the total number of transducer elements 38. In other embodiments, the number of control lines is equal to the total number of transducer elements 38. In some embodiments, 128 control lines 58 are used. Accordingly, the transducer 12 may include 128 transducer elements 38 in the central portion 40 and 32 transducer elements per lateral portion 44 for a total of 64 located in the lateral portions.

Figure 5A:
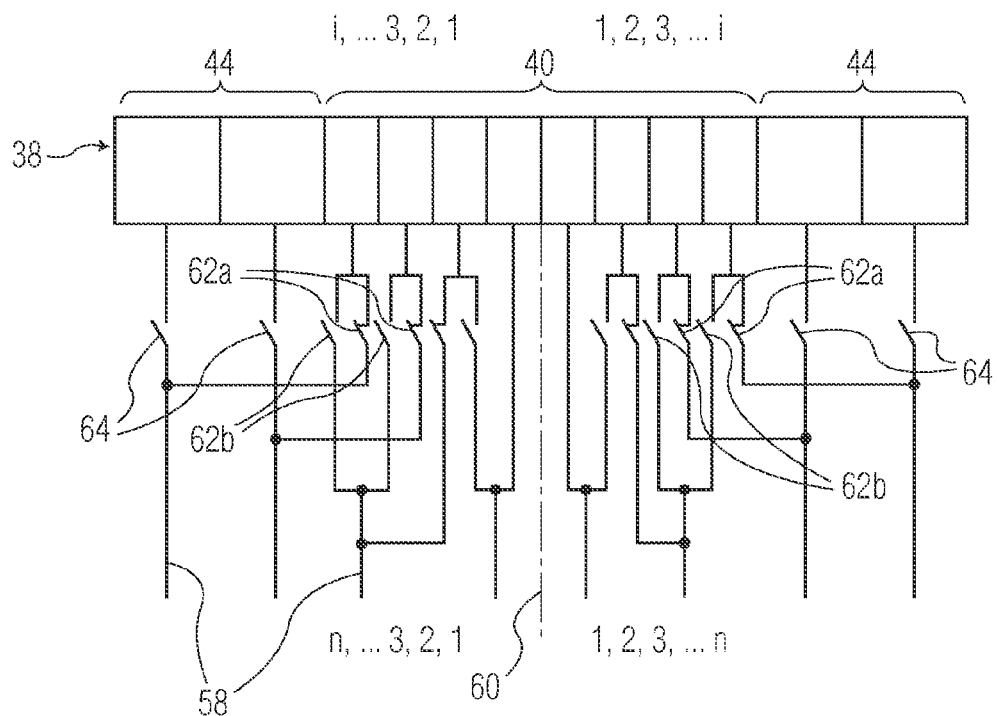
FIGS. 5A and 5B are schematic diagrams of a switch matrix coupling control lines to transducer elements in accordance with an embodiment of the present invention.
Figure 5B:
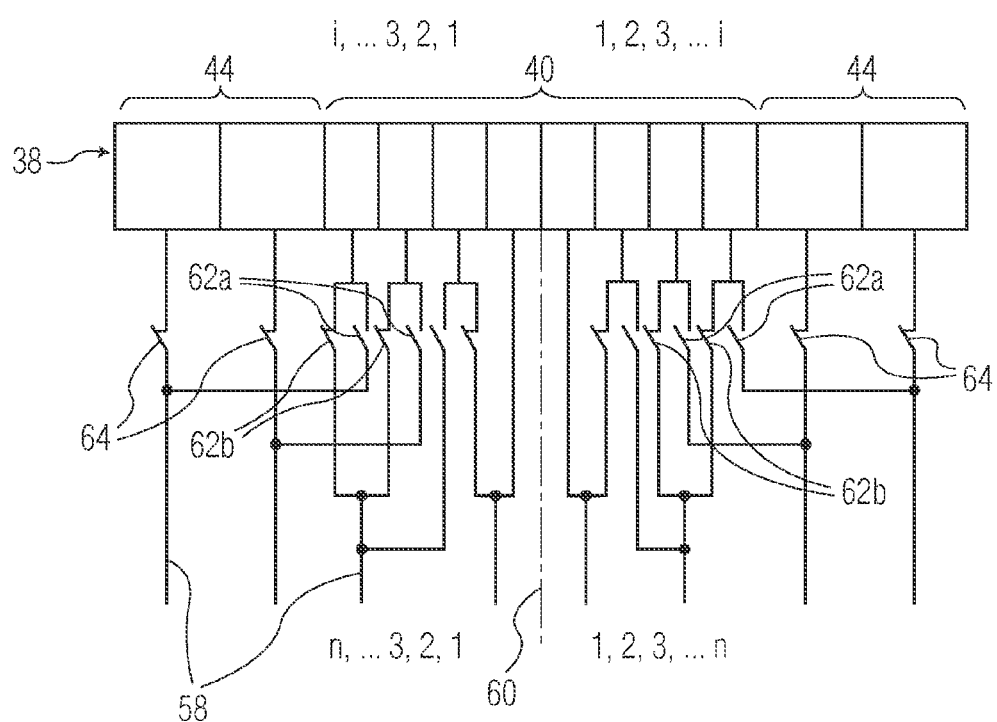

Referring to FIGS. 5A and 5B, in this embodiment the control lines 58 are coupled to the transducer elements 38 as illustrated. The illustrated coupling between the control lines 58 and the transducer elements 38 may be described mathematically by assigning each control line 58 a number (n) and assigning each transducer element 38 a number (i) corresponding to their position relative to the center 60 of the transducer 12. In sector mode, each control line n is coupled to transducer i=n of the central portion 40, as shown in FIG. 5A. In linear mode, each control line n is coupled to two transducer elements i=2n−1 and i=2n in the central portion 40 and transducer element i=N/2+n in the lateral portions 44, where N is equal to one half of the number of transducer elements 38 in the central portion 40, as shown in FIG. 5B.

Stated differently, each transducer element i in the central portion is coupled to control line n=i in sector mode and control line n=i−INT(i/2) in linear mode, where the INT( ) function returns the integer portion of its operand. Where i is equal to one, i−INT(i/2) is equal to one. Accordingly, transducer elements i=1 are coupled to control line n=1 in both sector and linear modes and no switching is needed. The remaining transducer elements i+1 to N of the central portion 40 are each coupled to the control lines 58 by two switches 62a, 62b, only one of which is closed at a time. Switch 62a is closed in the sector mode and couples transducer element i to control line n=i as shown in FIG. 5A. Switch 62b is closed in linear mode and couples transducer element i to control line n=i−INT(i/2), as shown in FIG. 5B. Switches 64 couple the transducer elements 38 of the lateral portions 44 to the control lines n=N+1 to n=N+M in linear mode, where M is the number of transducer elements 38 in an individual lateral portion 44. The switches 64 are closed in the linear mode and open in the sector mode.

Figure 6:
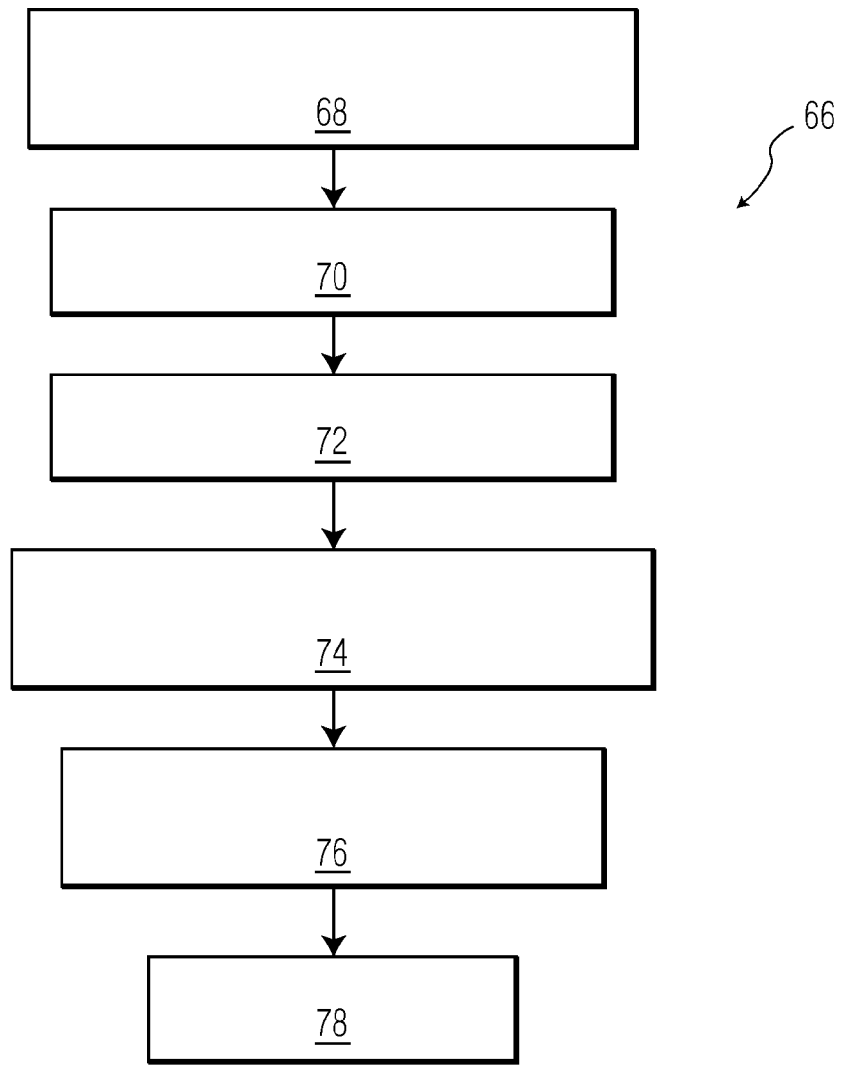
FIG. 6 is a process flow diagram of a method for using a dual mode transducer in accordance with an embodiment of the present invention.

Referring to FIG. 6, a method 66 for performing ultrasound scans may include coupling control lines to the transducer elements 38 of a central portion 40 of a transducer 12 at step 68. At step 70, one or more sector scans of a viewing area within a patient 14 are performed using the ultrasound system 10. At step 72, a user mode selection input is received from the user by means of a mode selection switch 20, graphical user interface, or other input means.

Where the mode selection input indicates selection of a linear scanning mode, the method 66 includes coupling pairs of transducer elements 38 of the central portion 40 to a portion of the control lines at step 74. At step 76, another portion of the control lines are coupled to the transducer elements 38 of the lateral portions 44. At step 78, a linear scan is performed. The steps of the method 66 may be reordered such that a user mode selection input indicating a sector mode causes the ultrasound system 10 to execute steps 68 and 70.

In order to properly image a viewing area within a patient 14, it is typically necessary to reduce air gaps between the transducer 12 and the patient's skin. This is typically accomplished by placing a sound-conducting gel on the patient's skin in order to fill gaps and provide a good sound-conducting layer between the transducer 12 and the patient's skin. When the front face 34 is convex, not all of the transducer elements 38 may adequately contact the patient's skin or the sound-conducting gel in some uses. For example, when imaging through a patient's ribs, the ribs may not allow the transducer 12 to be pressed into the patient 14 sufficient to make good contact with all of the transducer elements of the central portion 40. Accordingly, in some embodiments, the number of transducer elements 38 within the central portion 40 that are activated in sector mode may be reduced according to the number of transducer elements 38 in contact with the patient's skin or the sound-conducting gel.

Figure 7:
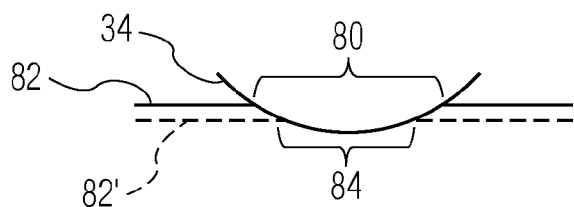
FIG. 7 is a schematic diagram of a curved transducer engaging a patient's skin in accordance with an embodiment of the present invention.

Thus, as shown in FIG. 7, where a first area 80 of the central portion 40 makes adequate contact with the patient's skin 82 then the transducer elements 38 within the area 80 will be activated to produce the steered beam. Where a smaller area 84 contacts the patient's skin 82', only the transducer elements 38 of the smaller area 84 are activated.

Figure 8:
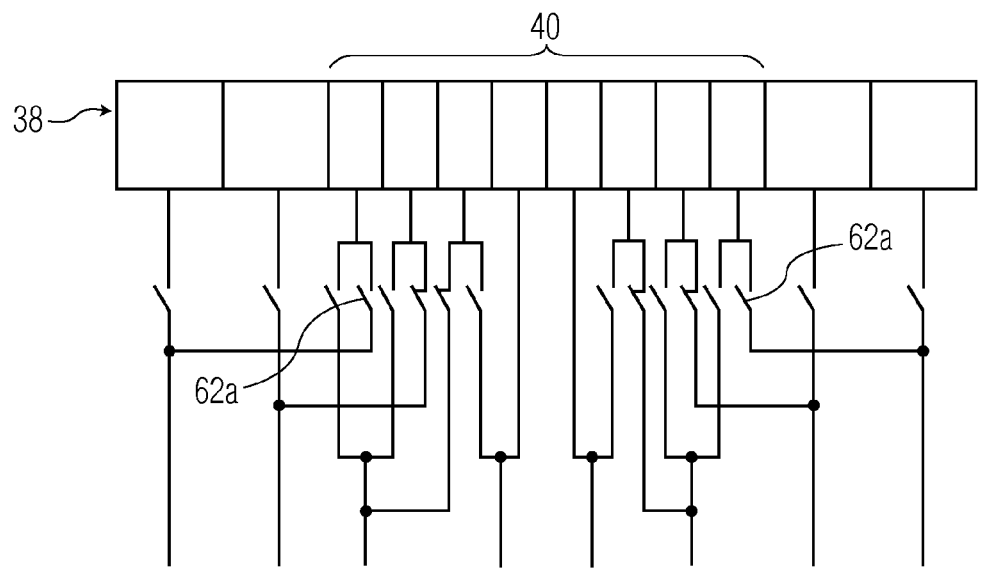
FIG. 8 is a schematic diagram of a switch matrix enabling a variable transducer aperture in accordance with an embodiment of the present invention.

Referring to FIG. 8, reducing the number of transducer elements 38 used in sector mode may include opening some of the outermost switches 62a in sector mode, as illustrated, such that the outer transducers 38 of the central portion 40 are not coupled to the beamformer 16.

Figure 9:
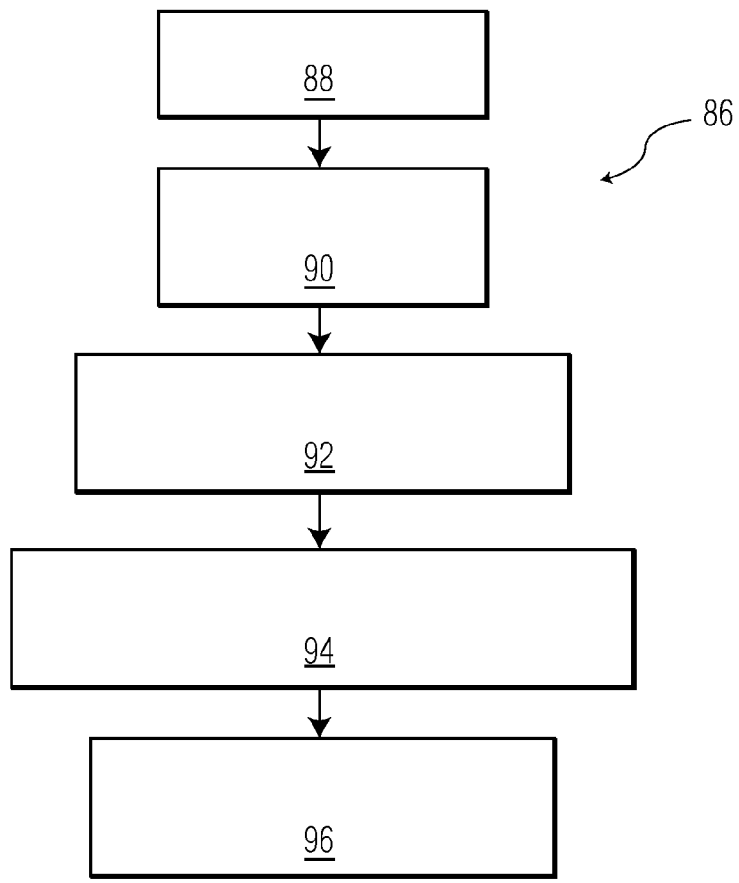
FIG. 9 is a process flow diagram of a method for using a transducer having a variable aperture in accordance with an embodiment of the present invention.

Referring to FIG. 9, a method 86 for accommodating different patient skin compliance may include performing an initial scan at step 88. In some embodiments, the initial scan includes sequentially emitting from each transducer element 38 such that an echo signal can be readily associated with each transducer element. At step 90, the output of the transducer elements 38 are analyzed to determine which of the transducer elements are not adequately engaged with the patient 14 or sound-conducting gel. Determining which of the transducer elements is not adequately engaged may include analyzing the echo signal received for each transducer element 38 and comparing the intensity of the reflected signal to a threshold to determine if adequate sound reception is occurring. At step 92, transducer elements 38 for which no signal or a below-threshold echo signal are received are identified as not adequately engaging the patient 14 or the sound-conducting gel. The identifying step 92 may be performed automatically or by an operator presented with an ultrasound image representing the echo signals from the initial scan. At step 94, the transducer elements 38 identified as not adequately engaging the patient or the sound-conducting gel are decoupled from the beamformer 16, reducing the active aperture for this scan. The decoupling step of step 94 may be performed automatically or by an operator. For example, an operator may turn a dial or interact with a graphical user interface element to indicate to the beamformer controller 18 which transducer elements 38 are to be decoupled or used in the active aperture. As an alternative to step 94, the beamformer 16 may be programmed to refrain from using signals in beamforming from elements identified as being inadequately acoustically coupled to the patient, rather than decoupling them from control lines. At step 96, one or more beam steered scans of the patient 14 is performed using the transducer elements 38 that are adequately acoustically coupled to the patient 14.

Although the present invention has been described with reference to the disclosed examples, persons skilled in the art will recognize that changes may be made in form and detail without departing from the spirit and scope of the invention. Such modifications are well within the skill of those ordinarily skilled in the art. Accordingly, the invention is not limited except as by the appended claims.

What is claimed is:

1. An ultrasound transducer operable in both the sector and linear scanning modes, comprising:
    a mode selection input for selecting either the sector or the linear mode;
    a curved array of transducer elements having a front face having a central portion and lateral portions on either side of the central portion; and
    a first plurality of transducer elements linearly disposed on the central portion and a second plurality of transducer elements linearly disposed on the lateral portions, the first plurality of transducer elements having a first pitch and the second plurality of transducer elements having a second pitch, the first pitch being substantially smaller than the second pitch,
    wherein the first plurality of transducer elements are operated in groups in the linear mode and individually in the sector mode.

2. The ultrasound transducer of claim 1 wherein the 1 wherein the first and second pluralities of transducer elements are disposed in a common plane.

3. The ultrasound transducer of claim 1 wherein the second pitch is about twice the first pitch.

4. The ultrasound transducer of claim 3 wherein the number of transducer elements of the first plurality is twice that of the second plurality.

5. The ultrasound transducer of claim 3 wherein the first and second pluralities of transducer elements are coupled to a switching matrix having a plurality of input lines and a plurality of output lines, each of the output lines being coupled to one of the transducer elements of the first and second pluralities, the switching matrix coupled to the mode selection input and having a first mode in which each of the output lines coupled to the transducer elements of the first plurality is coupled to one of the input lines and a second mode in which one of the input lines is coupled to each of the input lines coupled to the transducer elements of the second plurality and pairs of the output lines coupled to adjacent transducer elements of the first plurality are each coupled to one of the input lines.

6. The ultrasound transducer of claim 5 wherein the switching matrix is operable to receive an input in the first mode and wherein the number of output lines coupled to the transducer elements of the first plurality that are coupled to the input lines in the first mode corresponds to the input.

7. The ultrasound transducer of claim 1 further comprising a controller coupled to the mode selection input and coupled to the transducer elements of the first and second pluralities, the controller having a first mode in which signals are transmitted only by the transducer elements of the first plurality and a second mode in which signals are transmitted by the transducer elements of the second plurality and by pairs of adjacent transducers of the first plurality.

8. The ultrasound transducer of claim 7 wherein the controller is operable to receive an input in the first mode and wherein the number of transducer elements to which signals are transmitted in the first mode corresponds to the input.

9. The ultrasound transducer of claim 7 wherein the controller is operable to receive an input from a user corresponding to at least one of a first mode selection and a second mode selection, the controller further operable upon receiving the first mode selection to cause the transducer elements of the first and second pluralities to emit ultrasound beams radiating along lines passing through a first apex located behind the front face and operable upon receiving the second mode selection to cause the transducer elements of the first plurality to emit ultrasound beams radiating along lines passing through a second apex located in front of the front face.

10. The ultrasound transducer of claim 9 wherein the controller is operable to cause the transducer elements to emit ultrasound beams at an ultrasonic wavelength and wherein the first pitch is less than or about equal to one half the ultrasonic wavelength.

11. The ultrasound transducer of claim 9 wherein the second pitch is less than or about equal to the ultrasonic wavelength.

12. The ultrasound transducer of claim 9 wherein the mode selection input further comprises a mode selection button and wherein the transducer array is mounted within a hand grip including the mode selection button electrically coupled to the controller, wherein the controller is further operable to interpret user interaction with the mode selection button as at least one of the first and second mode selections.

13. The ultrasound transducer of claim 9 wherein the mode selection input further comprises a mode selection button and wherein the transducer array is mounted within a hand grip and the mode selection button is located on an ultrasound system user interface is electrically coupled to the controller, wherein the controller is further operable to interpret user interaction with the mode selection button as at least one of the first and second mode selections.

14. An ultrasound system, comprising:
a mode selection switch operable to select either a linear mode of scanning or a sector mode of scanning;
an ultrasound transducer including a curved array of transducer elements having a front face; and
a beamformer, responsive to the mode selection switch and coupled to the elements of the curved array, and operable in the linear mode to cause the curved array to transmit and receive all of the beams for an image in a normal orientation to the face of the array, and operable in the sector mode to cause the curved array to transmit and receive all of the beams for an image emanating from a common apex,
wherein the transducer elements of the central portion exhibit a finer pitch than that of the transducer elements on both sides of the central portion.

15. The ultrasound system of claim 14 wherein in the linear mode the curved array is operated as a linear array and in the sector mode the curved array is operated as a phased array.

16. The ultrasound system of claim 15 wherein, in the linear mode, an active aperture for each beam is shifted along the face of the array from beam to beam, and in the sector mode, the same active aperture of transducer elements is used for phased array beam steering of each beam.

17. The ultrasound system of claim 14 wherein, in the sector mode, the active aperture of the transducer comprises only transducer elements located in a central portion of the transducer array; and
in the linear mode, the active aperture of the transducer comprises transducer elements located in the central portion of the transducer array and transducer elements located on both sides of the central portion.

18. The ultrasound system of claim 17 wherein, in the linear mode, the transducer elements of the central portion are operated in pairs.

* * * * *